United States Patent [19]

Petersen et al.

[11] Patent Number: 4,802,367

[45] Date of Patent: Feb. 7, 1989

[54] TENSILE TEST CONTROLLER

[75] Inventors: Niel R. Petersen, Minnetonka; David G. Chasco, Bloomington, both of Minn.

[73] Assignee: MTS Systems Corporation, Eden Prairie, Minn.

[21] Appl. No.: 147,070

[22] Filed: Jan. 25, 1988

Related U.S. Application Data

[63] Continuation of Ser. No. 939,749, Dec. 9, 1986, abandoned.

[51] Int. Cl.$^4$ .............................................. G01N 3/00
[52] U.S. Cl. ..................................................... 73/805
[58] Field of Search .................. 73/826, 834, 806, 816, 73/811, 788, 805

[56] References Cited

U.S. PATENT DOCUMENTS

| | | | |
|---|---|---|---|
| 3,304,768 | 2/1967 | Naumann et al. | 73/816 |
| 3,374,665 | 3/1968 | Preston | 73/805 |
| 3,826,902 | 7/1974 | Claxton et al. | 73/834 |
| 3,898,874 | 8/1975 | Wawra | 73/805 |
| 4,235,114 | 11/1980 | Mohler | 73/826 |
| 4,480,482 | 11/1984 | Henry et al. | 73/805 |
| 4,572,001 | 2/1986 | Saimoto et al. | 73/805 |
| 4,618,267 | 10/1986 | Burke et al. | 73/826 |

FOREIGN PATENT DOCUMENTS

| | | | |
|---|---|---|---|
| 0072043 | 5/1982 | Japan | 73/826 |
| 1006970 | 3/1983 | U.S.S.R. | 73/826 |

OTHER PUBLICATIONS

Jerram, "An Axial Servo-Controlled High Strain Fatigue Machine", J. Phys. E. (GB) vol. 3, No. 7, Jul. 1970.

Pelloux et al., "Hydraulic Tension-Compression Fatigue Machine", The Review Of Scientific Instruments, vol. 35, No. 11, pp. 1564–1567, Nov. 1964.

*Primary Examiner*—Stewart J. Levy
*Assistant Examiner*—Robert R. Raevis
*Attorney, Agent, or Firm*—Kinney & Lange

[57] ABSTRACT

A tensile test controller has both load and stroke control circuits that are coupled together to permit tensile testing a specimen while controlling the load on the specimen, and when the specimen yields, for safely and smoothly switching to stroke control to complete the test and break the specimen. The controller has circuits which provide control over the velocity of the actuator as the specimen yields, and to prevent the specimen from being placed into compression, and also to sense the plastic specimen deformation a desired amount after it has yielded, but before the stroke control function is activated. Simplified supervisory gates are used to insure that the appropriate signal is controlling the test.

18 Claims, 4 Drawing Sheets

TENSILE TEST CONTROLLER

CROSS REFERENCE TO RELATED APPLICATION

This application is a continuation of my copending application Ser. No. 06/939,749, filed Dec. 9, 1986 for Tensile Test Controller, now abandoned.

BACKGROUND OF THE INVENTION

1. Field of the Invention

The present invention relates to control circuit improvements for tensile test controllers. At the present time, servo controlled testing systems are well known, and are used for various types of tests. These include servo controlled actuators that perform fatigue tests, and also servo controlled actuators for tensile testing of specimens to determine material characteristics.

2. Description of Prior Art

Servo controlled test systems operate by minimizing an electronic error signal, so that a programmed loading can be achieved. In elementary form an electrical command input signal is provided, generally in the form of one or more monotonic ramp signal(s) having a desired voltage level relative to time, and then providing a feedback signal(s) from the load frame being operated, which is compared with the input signal at an input summing junction so that any error between the desired command signal and the feedback signal will result in a change in the drive to the servovalve and thus a change in the actuator operation.

The servoloops are commonly operated in "load control", that is, the command signal indicates the load which is desired to be exerted by the actuator and the feedback signal from a load cell or other force sensing transducer indicates the actual load exerted. Another common mode of servoloop operation is "stroke control" in which the input command signal represents desired displacement of the actuator, and the feedback would be from a stroke or displacement transducer such as an LVDT. When testing specimens in tensile tests, it is also common to have an extensometer mounted on the specimen which measures the strain on the specimen, and in such instances it is normal to alternatively utilize the strain feedback signal from the extensometer to control the actuator as a function of a programmed or commanded strain. In other words, a command input signal will indicate the amount of desired strain in the specimen across a period of time, and the strain feedback signal is then used for controlling the actuator through servo controls.

When testing a specimen in tension, it sometimes happens that the extensometer will slip, or become loose, or a wire could break, and if that happens the testing system essentially is uncontrolled if the system happens to be operating in strain control.

When the system is operated initially in load control on a test specimen, as the specimen starts to yield, the specimen reacted loads can drop off substantially, causing undesired accelerated straining of the specimen. Depending on the specimen characteristics, there may be undesired strain acceleration during specimen post yield when ramping initially in a straight load control.

The present invention solves some of these problems by providing an automatic control wherein load and displacement are used in sequence, and also in one form of the invention, cascade strain control, for preventing unwanted excursions of the actuator in case the strain feedback signal is lost. The use of load and displacement control in sequence permits achieving accurate control of the test even during specimen yielding, and when the elastic and plastic portion of the test is known to be complete, final accelerated fracture of the specimen can occur.

Various circuits have been advanced for driving (controlling) servo valves, and various linearization schemes also have been utilized. Bumpless control transfer circuits are used, for changing from one control mode to another, and all of these are operated using essentially the same types of controls as that shown herein with the exception that the present device has the cascade control for fail-safe operations in extensometer control testing.

SUMMARY OF THE INVENTION

The present invention relates to a tensile load controller coupled to a stroke control loop in a manner which insures bumpless mode switching, and also provides simplified safety factors in a supervised control system. The present circuitry retains control of the actuator after a tensile test specimen has yielded, to provide for safe, efficient operation for completion of the test to comply with ASTM standards and subsequently rapidly and safely fracturing the specimen.

The tensile test controller of the present invention has, in one form of the invention, two standard modes of operation, optionally accomplished in cascade form. One is initial load switching to displacement control and the other is initial strain switching to displacement control. Load control is used for cascade operation whenever the system hydraulics are first turned on, and feedback signals are sensed so that the control system can be automatically switched into cascade control when either the load-displacement cascade tensile control switch is operated or when the alternate strain-displacement cascade control switch is operated. In the load-displacement cascade mode of operation, the system cascade load control will deform a specimen at a preset constant loading rate, that is a certain load per unit of time, while permitting only a constant or decreasing actuator velocity. When the specimen begins to yield the cascade control system will be latched at its minimum displacement ramp velocity, to avoid rapid excursions or accelerations of the actuator as the specimen load reaction capability drops off during specimen yield. This latched actuator velocity is maintained through yield (and until the required elongation beyond yield is reached). The controls will then change to conventional stroke control allowing the actuator velocity to be increased to fracture the specimen in a minimum allowable time. When the module detects specimen fracture, the actuator is stopped in a conventional manner.

Load or strain cascade control will remain in effect only if the main hydraulic power is left on. If the hydraulic system is turned off the system will return to conventional load control for initialization for another start up cycle.

In the strain-displacement cascade mode of operation in the first form of the invention, the system also will initially start in load control when the hydraulic power supply is first turned on, and during initial post turn on operating conditions the strain-displacement cascade control will track the differential between the strain and displacement controller outputs. Upon selection by the operator the system will switch to cascade strain control and strain the specimen at a preset rate, wherein the strain will be increased per unit time. After suitable straining, the control circuit will permit changing into a conventional displacement control at the same stroking rate, removing the need for strain feedback, allowing the extensometer to be removed while the test is still progressing. Also, the actuator velocity can be externally controlled to smoothly increase to a second rate in the same manner that was previously mentioned in relation to the load-displacement control.

The second form of the invention usable for load-stroke tests is simplified in that it requires no cascade control, using only load and stroke controllers with load and stroke feedback signals for operation. The test is carried out initially in load control with a minimum latch velocity signal provided as a control override to prevent the actuator from sudden retraction acceleration after yield of the specimen while under load control. The stroke controller is coupled through a gate arrangement which switches the servovalve drive source to the stroke controller for system control after yield, with the minimum latch velocity signal protecting the system until the stroke controller is placed in conventional ramp program for accelerated fracture.

A further modification provides plastic strain offset voltage sensing that automatically insures that the specimen is elongated sufficiently beyond yield to comply with ASTM test specifications. After the desired plastic strain offset is detected, the stroke control can be used for fracturing the specimen.

Suitable reset operations are provided for returning to the original starting position.

An electronic anti-compression circuit is disclosed for providing a signal which positively prevents the loading the actuator in a direction that would cause compression in a specimen despite operator errors, etc., to avoid accidental damage to equipment.

DETAILED DESCRIPTION OF THE PREFERRED EMBODIMENTS

Figure 1A:
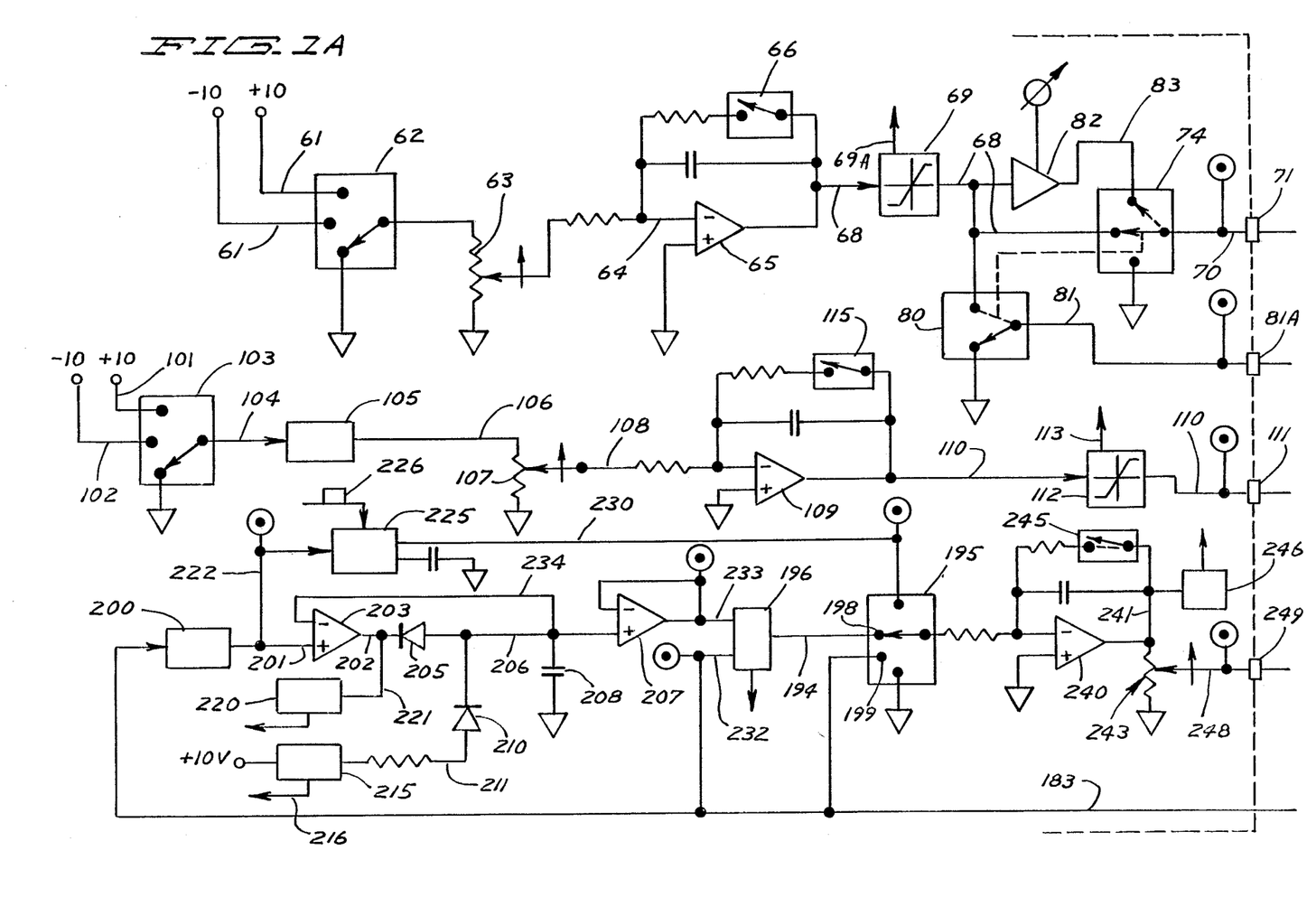
FIG. 1A and 1B are a schematic representation of a test system made according to the present invention.
Figure 1B:
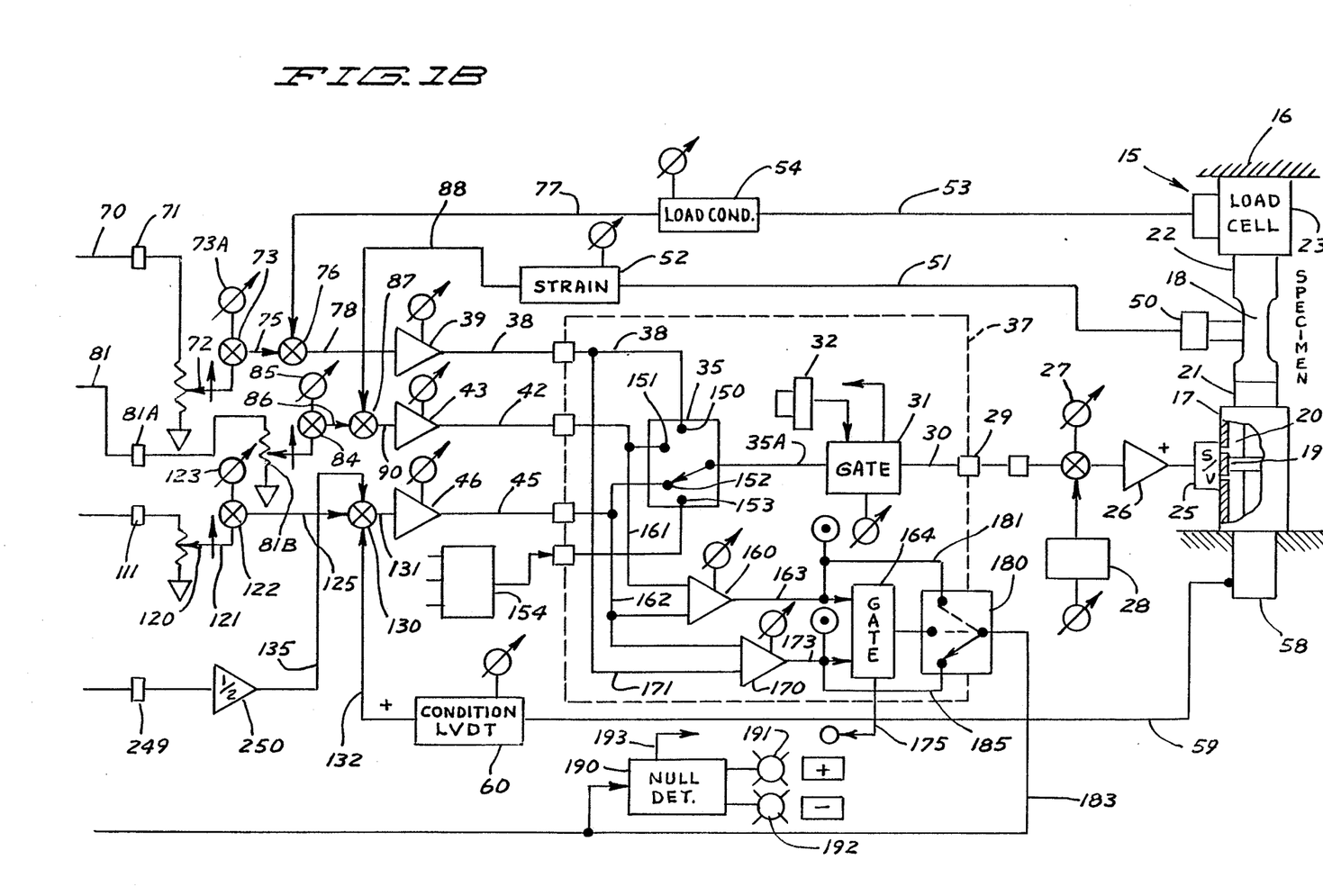

Reference is first made to FIG. 1B, for illustrating one end use for which the present invention wa developed. Illustrated schematically on the right hand side of FIG. 1B is a specimen test arrangement indicated generally at 15, which includes a load frame 16, on which an actuator 17 is mounted in a normal manner for tensile testing a specimen 18. The actuator has a piston 19 and a piston rod 20. The piston is double acting, that is, it can be operated for movement in both directions along the axis of the actuator. The rod 20 is connected to a specimen grip 21, which is shown schematically, to hold one end of the test specimen 18. The second end of the test specimen 18 is held in another suitable specimen grip 22, and through a load cell 23 is supported on the upper cross head of the load frame 16. Load frames are well known, and the frame 16 is shown only schematically.

A conventional servovalve 25 is utilized for controlling the actuator 17 by directing hydraulic fluid flow from a pressure source to the actuator to cause movement of the piston 19. A valve driver amplifier 26 is utilized for providing an amplified signal to the servo valve, and the normal balance control 27 and valve dither control 28 can be provided at the input of the amplifier 26.

The amplifier input signal is received from an anti-compression gate 31 through a line 30 and a connector 29. The gate 31 is set so it normally will pass all normal controller signals until such time as the alternate controller signal from the circuit of FIG. 3 places the specimen under less compression or more tension than the signal on line 35A, at which input time the gate 31 intercepts the input signal, as will be explained in connection with FIG. 3. The gate 31 also has an override manual button 32 that permits moving the actuator in a direction to compress the specimen when initially loading and the like.

A load switch 35 is connected to the input of gate 31 through line 35A and switch 35 is made so that it can be set to select three different types or categories of servovalve drive, at certain of its terminals, and also has a position to provide external signals to the gate 31 if desired. The three control drive signals are commonly based on load (force), specimen strain, and actuator displacement or stroke.

A load control drive signal is provided along a line 38, from a load control error signal amplifier 39. A strain control drive signal is provided along a line 42 from a strain control error signal amplifier 43 and a displacement or stroke control drive signal is provided along a line 45 from a stroke control signal amplifier 46.

The inputs to the amplifiers 39, 43 and 46 are derived conventionally for the load and strain controls, but the stroke or displacement amplifier is made to alternately provide for a cascade integrator control which will in turn include either a function of the load feedback signal, or a function of the strain feedback signal from an extensometer 50 (shown only schematically) that is coupled to the specimen 18 to sense strain in the specimen, and which provides a feedback signal along a line, 51 that is proportional to the strain in the specimen with respect to a zero reference signal. There are feedback signals needed for cascade load-displacement or strain-displacement control, as previously stated.

The strain feedback signal on line 51 is passed through suitable conditioning circuitry, which converts the signal 51 to the appropriate form and level for use with the other circuitry, and this is shown schematically at 52, in that it is a conventional circuit.

Likewise, the load cell feedback signal is provided along a line 53 through suitable conditioning circuitry 54.

The stroke or displacement feedback signal is derived from an LVDT or displacement transducer indicated at 58, which is a conventional displacement transducer associated with the actuator 17, and conventionally used in servo hydraulics. The stroke feedback signal is fed along a line 59 through suitable signal conditioner circuitry 60. The signal conditioner 60 is a circuit that provides an AC carrier signal, but which provides a DC output for feedback purposes.

The conditioner circuits 52 and 54 are straight DC signal conditioner circuits.

Referring now to FIG. 1A, a source of ramp generator rate command, selectable to be either plus 10 volts or minus 10 volts is provided on lines 61A and 61, respectively. A switch 62, which is a load input switch can be connected to one or the other of these lines depending on the assigned polarity of the load signal desired. The switch 61 also can be connected to circuit common. Switch 62 has an output connected to a potentiometer 63, which is a rate control for scaling the ramp rate. The potentiometer wiper is connected through a resistor to a line 64 and then to an inverting input of an integrator amplifier 65. The output of integrator 65 is connected to a reset switch 66 in a summing loop back to line 64. The switch 66 is closed only when the integrator is to be reset. The integrator 65 is made to provide an input program or loading ramp along a line 68. The signal on line 68 is illustrated graphically in the box 69 which represents an abnormal saturation limit detect circuitry. A line 69A can be provided to indicate that a saturation limit has been reached. The ramp signal is provided along the line 68, to an amplifier 82 and to a terminal of a switch 74 that has three positions. When the switch arm of switch 74 is in its centered position as shown in solid lines, line 68 is connected to the load input line 70 and through a connector 71 to the rest of the circuitry that is shown in FIG. 1B, including a span adjustment potentiometer 72, a summing junction 73, that compares the signals from the span potentiometer 72 an a variable input gain potentiometer 73A, to provide an output command signal along a line 75 to a summing junction 76. The summing junction 76 receives a load feedback signal along a line 77 from the load conditioning circuitry 54. A load control error signal is provided along a line 78 from summing junction 76 to the load error signal amplifier 39, and thus through the switch 35 to provide a load control drive signal to the servovalve 25 when the switch 35 is in its proper position.

The input ramp signal illustrated by graph 69 in FIG. 1A along line 68 also is used for an input to the strain control loop. A switch 80 (FIG. 1A), is normally in its solid line position as shown when switch 74 is in its centered position to provide the load command signal along line 70. The switch 80 is logically ganged to switch 74 and when switch 80 is in its dotted line position, switch 74 also is moved to the dotted line position shown in FIG. 1A. The switch 81 then connects line 68 to a switch output line 81. The line 68 remains connected to an amplifier 82 which has an output line 83 that is connected to the terminal of switch 74, which, when switch 74 is in the dotted line position, connects the amplifier 82 to the line 70 for providing a signal that will be used for determining when the strain control causes loads to be applied which are not in reasonable scale to those normally expected, indicating a fault is in the strain control system. For example, when the load signal indicates there is serious discrepancy with respect to the strain signal, interception of strain control may be necessary.

The line 81 is connected through a connector 81A and through a span adjustment pot 81B which has an output line connected to an input of summing junction 84 that also has an input from a set point controller 85. The summing junction 84 sums the input signals and provides an output along a line 86 to a summing junction 87 which sums the signal on line 86 with the strain feedback signal from the signal conditioning circuitry 52. The strain feedback signal from the circuit 52 is provided along a line 88 to the summing junction 87, and the summing junction 87 provides an output strain error control signal along a line 90 to the strain signal amplifier 43, which is connected to load switch 35.

The third mode of control of the actuator is stroke control, and the normal rate command input is from plus 10 and minus 10 volt sources along lines 101 and 102, respectively to a selector switch 103 (FIG. 1A). The output along a line 104 from switch 103 is fed through a conventional slew limiting circuitry indicated schematically at 105 which controls the rate of change to insure that the stroke velocity command signal is not changing too rapidly. The output of the slew rate circuit along line 106 is provided through a rate scaling potentiometer 107 to a line 108 that is connected to an integrating amplifier 109. The signal on line 108 is integrated and the integrator output signal is provided on a line 110. The signal on line 110 is the integral of the signal on line 108 from the potentiometer 107. The form of the integrated signal on line 110 is illustrated in a limit detect circuit represented at 112. A line 113 can be taken off circuit 112 for indicating that unintended stroke command saturation or ramp limit has been reached. The signal along line 113 is to indicate that the limit has been reached. A similar indicating line can be provided for the previously described detect circuit 69 as well. A feedback reset switch 115 is provided across the integrating amplifier 109, and it is closed only when the integrator circuit is to be reset.

The output along line 110 is connected through a connector 111, to a span potentiometer 120 (FIG. 1B), which provides an output along a line 121 to a summing junction 122 that sums the signal on line 121 with a stroke set point signal from an adjustable potentiometer 123. The summing junction 122 provides a stroke error output on line 125 to a second control summing junction 130 which has an output line 131 that feeds directly into the stroke control error amplifier 46.

The summing junction 130 has two additional inputs, in addition to the input from the command signal on line 125, including a feedback signal line 132 that is connected to the conditioner circuit 60 providing a stroke or position feedback signal. When the test system is operating on conventional stroke control, the command signal on line 125 and the feedback signal on line 132 are summed to provide an error signal on line 131 which is used for controlling the servovalve 25 when coupled through switch 35.

However, in the present device an input line 135 is also connected to the summing junction 130, and the line 135 provides for the cascade control inputs.

The cascade controller includes the elements shown within dotted line 37, including the gate 31 and the load switch 35. The switch 35 is a manual switch that has a switch arm which can be switched to a terminal 150 for load control, a terminal 151 for strain control, a terminal 152 (as shown) for stroke control, or a terminal 153 which leads to a separate input connection arrangement 154 which may provide a desired external operating signal. The box 154 represents an entirely different servo controller that would operate through the switch 35 to control the servovalve with a suitable feedback provided.

An amplifier 160 is connected as a differential amplifier that has one input connected to a line 161 that in turn is connected to line 42, which carries the strain control drive signal from amplifier 43. The second input of comparator 160 is connected to line 162 which provides the stroke control drive signal from line 45. The analog output of amplifier 160 will be the difference between the amplified strain and stroke control signals. The output of the amplifier 160 on a line 163 is fed to a gate 164 that is switched from one state to another depending on the signals on the line 163 at one input to the gate 164 and the signal on a second input to the gate, which is connected to the output line 173 of a second differential amplifier 170 associated with the gate. The second amplifier 170 has a first of its inputs connected to line 162 and thus to line 45, and a second input of amplifier 170 is connected to a line 171 that is in turn connected to line 38. The output of amplifier 170 is thus the difference between the load control drive signal on line 38 and the stroke control drive signal on line 45.

As stated, the output of amplifier 170 is the difference between the stroke and load controller drive outputs. Amplifier 160 has an output which is the difference between stroke and strain controller drive outputs. The analog gate 164 is used to ascertain that the load increases at no more than a certain set rate whenever the system operates in strain control. If the load increases too fast, and gate 164 changes state, the extensometer control is considered invalid, and appropriate shutdowns are initiated.

The gate 164 comprises a strain supervision gate that provides an output along a line 175 to indicate the state that it is in. The state of gate 164 is controlled by the relative magnitudes of the signals from the amplifiers 170 and 160. A switch 180, which is a three position switch, is logically ganged to switch 74 and thus switch 80, and has a position wherein an output line 183 is connected to a line 181 and thus to the line 163, which carries the output signal from amplifier 160. Thus line 181 carries an analog signal from the output of amplifier 160 which bypasses gate 164. The output line 183 from the switch 180 leads to the cascade control integrator through suitable switches as will be described.

When switch 180 is in its second or center position as shown in solid lines, it is connected to the output of the gate 164 and in a third position, the switch 180 is connected so that its output line 183 connects to a line 185 that is in turn connected to analog output line 173 of amplifier 170.

The analog signals that are carried on line 183 are thus a function of the type of control and/or central supervision that is desired. Because the switch 180 is ganged to the switch 74, it changes position between lines 181 and 185 when switch 74 changes position between strain and load control.

A null detecting circuitry is indicated generally at 190, and it provides an output indication whether or not the signal on line 183 is zero, for operator control, or for interlock purposes. Signal lights 191 and 192 are shown for plus and minus conditions on line 183 respectively, and an output line 193 is provided to drive a suitable signal indicator.

The line 183 is shown in FIG. 1A coupled to an input terminal 199 of a cascade control switch indicated generally at 195. The switch 195 has additional input terminals that will be further identified. The line 183 also connects to an input of a gate 196 that has an output connected through a line 194 to the center terminal 198 of switch 195, and line 183 connects through a low pass (10 hz) filter 200, which has an output line 201 connected to a positive input terminal of an amplifier 203 that is connected as an integrator. The output line 204 of integrator amplifier 203 is connected through a reverse conducting diode 205 to a line 206, that in turn is connected to the positive input terminal of an amplifier 207, which also is connected as an integrator. The line 206 is connected back to the inverting input of amplifier 203 by a line 234. A capacitor 208 is connected to line 206 to provide a reference signal for the minimum velocity detector function.

Line 206 has a diode 210 connected to it, and the diode is connected to a line 211 leading to a yield detector circuitry 215 that has an output line 216. The yield detector circuitry can be a logic circuit that determines when load and strain are no longer proportional.

A most positive state detector circuit 220 is connected through a line 221 to the output line 202 of amplifier 203 to line 221 to detect "hard over" output of amplifier 203, sensing that a minimum velocity has been achieved, and that acceleration is occurring. Line 201 is further connected through a line 222 to a sample and hold circuit 225, that is operated by a hold signal 226, and will hold the sampled velocity signal on line 201 and provide it along an output line 230 to a terminal 231 of switch 195.

The line 183 is connected to the analog gate 196, at an input line 232 of this gate 196, and a second input of the gate 196 is connected to the output line 233 of amplifier 207. Gate 196 is a minimum velocity detection gate connected to cascade integrator 240.

The cascade control selection switch 195 is shown in its solid line position connected for cascade load-displacement control. Switch 180 is connected to line 185, so the signal on line 183 is the difference of the load control signal and the displacement control signal. This signal then is fed by gate 196 through switch 195 to a cascade control integrator amplifier 240, which has its output line 241 connected through a range set control potentiometer 243. Potentiometer 243 is made so that it will provide a signal across the elastic range of the specimen being tested, and can be adjusted for providing outputs for different types of materials that are being tested.

A reset switch 245 is provided for resetting the integrator 240, and it is closed only when the unit is to be reset. A limit sensing circuitry 246 is connected to the output line 241 as well, and provides an output along a line 247 that indicates when saturation limits have been reached. The output line 248 of potentiometer 243 is connected through a connector 249 to an amplifier 250 (FIG. 1B) that is scaled for providing a signal of appropriate level. The output of the amplifier 250 is provided on line 135 that leads to an input of the displacement summing junction 130.

Initially in a cascade load-stroke test, the normal position of gate 196 is with the signal on line 232 (and thus line 183) being selected because it is higher than the input from the amplifier 207. The integrator tracking is then accomplished through summing junction 130 wherein the cascade integration output signal nulls the signal from the amplifier 170 generalizing the necessary displacement command signal to track the actual displacement feedback signal. The input to the tracking integrator on the output of switch 195 then is representative of the actuator velocity.

When the yield logic 215 output becomes high, the minimum velocity detector circuits comprising amplifier 203 and diodes 205 and 210, capacitor 208, and amplifier 207 will cause gate 196 to select that signal on line 233 to provide a fixed velocity command until completion of the test.

When the test system is to be controlled in cascade strain-displacement control, the switch 74 will be moved to its dotted line position so that line 70 is connected to the line 83, and switch 80 will move to its dotted line position so that the command signal is on line 81. The switch 180 would move under logic control to connect the output line 183 to the line 181. The output of amplifier 160, which would be a function of the strain signal and the displacement signal, would then be fed through line 183, and the switch 195 would connect to the terminal 199 so that the tracking velocity signal for the strain-displacement cascade integrator would be connected directly to the input of amplifier 240.

Amplifiers 160 and 170 also provide information relating to what is occurring at the specimen, because they compare the load controller drive signal with a displacement controller drive signal and the strain drive signal with the displacement drive signal. For example, if the load control drive signal, which is the signal on line 38, calls for less tension loading on the specimen based on an anticipated fraction of the strain command as determined by the coefficient set at amplifier 82 than that which the strain controller calls for, there is an indication, then, that there is something wrong with the extensometer, and the strain feedback signal may not be correct. When this occurs, the gate 164 will change state because the output on line 42 will be less than that on line 38, and they are both being compared to the stroke control signal, so there will be different states at the amplifiers 160 and amplifier 170 outputs, indicating that there is something wrong with the strain.

When initializing the system, the operator will have "run" buttons, permitting the operator to select the desired mode of operation. The switches 66, 115, and 245 will be closed to their dotted or reset position before the run button is pushed. Likewise, switch 62 and switch 103 will be in their ground or circuit common position as shown. Switch 35 will be connected to the terminal 150 by logic circuits (or manually) so the servo-valve will be controlled only by the load controller and will start from zero so there is no sudden loading upon hydraulic turn-on. The only safe way to start up the system is to start in load control with zero load being programmed on the ramp generator. The closing of the reset switches 66 and 115 resets the ramping integrators that they are associated with. Tracking cascade integrator 240 will initialize itself in that there is zero differential between the stroke controller output 45 and the load controller output 42, allowing a smooth switch of servovalve command signal 35A to be made at switch 35. Likewise, switch 180 will be in its lower (solid line) position to operate in load-stroke control once the initialization sequence is complete. Since switch 180 is ganged to switch 80 and switch 74 by logic circuits, switch 80 will be in its lower solid line position and switch 74 is in its centered position as shown. Manually pushing the run button to load-stroke control will open switches 66 and 245 and will move the switch 62 to select either the −10 volt or +10 volt setting depending on the convention that is being used. (Normally, retraction of the actuator will be done with a negative voltage.)

Additionally, switch 195 will be in position engaging terminal 199, so that it receives a signal from switch 180 that is representative of the amplified differential between the load controller drive signal and the stroke controller drive signal as determined by the differential amplifier 170. The signal, then, that is received by switch 195 will be applied to the amplifier 240 so that the cascade controller will initialize itself and apply the signal to summing junction 130. The cascade control integrator output is summed at the summing junction 130 with the stroke controller output and the stroke feedback. The switch 180 is providing a signal that is the differential between the output of the stroke control amplifier 46, which is fed by summing junction 130, and the load controller output.

Before the load ramp command signal has started, the servo-valve receives its drive from the load controller output and the cascade tracking integrator output signal settles down quickly to match the actual actuator position. When initialization is complete, which can be determined by a time delay or by an indicator, the output signal from null indicator 190 is at null, and the system is ready to be entered into load-stroke cascade control.

The switch 35 may be moved by logic circuits or manually to position 152, and switch 195 is moved to terminal 19B, and the test system is then in cascade load-stroke control. The stroke controller will be the control loop directly operating the actuator and the load controller will program the stroke controller by the signal to differential amplifier 170 and then through switch 180, line 183, gate 196 and switch 195 to the cascade integrator. The test is then underway under load-stroke cascade control.

As the specimen starts to yield, the load feedback indicates that the load starts to drop off and the load error signal becomes greater to attempt to increase specimen tension and thus increase velocity of retraction of the actuator. The gate 196 prevents the velocity of the actuator from running away and causing excessively rapid specimen deformation. The capacitor 208 has been charged by the circuitry to a value to represent a latched minimum velocity of the actuator which occurred during initial loading. The signal on line 183 will be calling for more velocity. When the signal on line 183 calls for a velocity that exceeds the minimum sensed actuator velocity represented by the signal on capacitor 208, gate 196 will detect that the signal on line 233 is less negative and will switch to provide the minimum latched velocity signal to the cascade integrator until the specimen test is completed. The gate 196 will select the signal on line 183 so long as it requires less velocity than the signal on line 233, but will not permit the velocity to exceed that set by the signal on capacitor 208.

Capacitor 208 is fully charged at each reset of the system to provide the maximum or greatest allowable minimum velocity signal. Once the logic circuit 215 indicates that the specimen has yielded, the displacement ramp command signal may be increased by the output from ramp generator 109 to quickly break the specimen.

The system permits the operating or run modes to be operator selected from load-to-stroke control, as just described, to an alternate control utilizing the feedback signal from the extensometer as the initial controlling parameter. In order to do this, the manual run switch can be operated to move the switch 180 to connect to line 181, providing a signal that is strain-stroke supervised feedback. At the same time, switch 74 will move to its dotted line position, and switch 80 will move to its dotted line position as well to provide the necessary strain signals. With switch 180 connected to line 181, the system will operate as previously explained in relation to load-to-stroke control. Upon hydraulic start up, there will be a load control signal coming through the amplifier 82 and switch 74.

The switch 180 can be moved to its centered position, where it is connected to the output of the gate 164. In this position, the signal along line 183 will normally be the signal on line 163, which will be the same signal as on line 181, while the gate 164 provides a supervisory function to determine that the extensometer is operating properly. The gate 164 compares the signal at line 163 with the signal at line 173, which is a function of the difference in the load and stroke error signals. Analog gate 164 is a circuit comprising a pair of diodes that select the most positive signal, and if for example, the extensometer is left in its locked position (extensometers generally have a position that is pinned to prevent the extensometer from moving at all, and thus avoid damage when the extensometer is not in use) the error signal from the strain controller would become large because the extensometer would not be providing feedback indicating any strain and the input control would then be calling for additional retraction of the actuator. This would mean that the servovalve drive signal would become very negative, and the gate 164 would detect this, because it is set to pass the most positive drive signal from the lines 163 and 173.

Switch 74 will be carrying a load signal through the amplifier 82, to provide a signal to line 171 that is compared with the signal on line 162 providing an output on line 173 that would be proper for load-stroke control If the extensometer is not operating, the gate 164 will switch over to an appropriate signal to prevent specimen damage and to ensure that the test intended.

Again, if desired, switching switch 180 to line 181 will avoid the supervisory gate and be controlled in straight strain-stroke cascade control.

The operator also has an extensometer remove button, whereby the signal on line 183 can be held for the strain-stroke control mode, depending on the state of switch 180. A sample and hold circuit 225 is used to latch the actuator velocity during a strain ramp, so that the extensometer can be removed without a deformation transient. The hold button will operate the sample and hold circuit 225, and at the same time will cause the switch 195 to switch to its uppermost position to sense the signal on line 230 and provide the signal that is available at that time from line 183 to the cascade integrator system 240-243. The low pass filter 200 will ensure that the instantaneous sample signal on line 183 is not contaminated by noise, so that the held velocity signal will be representative of the appropriate control signal desired.

Both analog gates 164 and 196 can be diode logic circuits that select the highest signal, and these circuits are well known.

Figure 3:
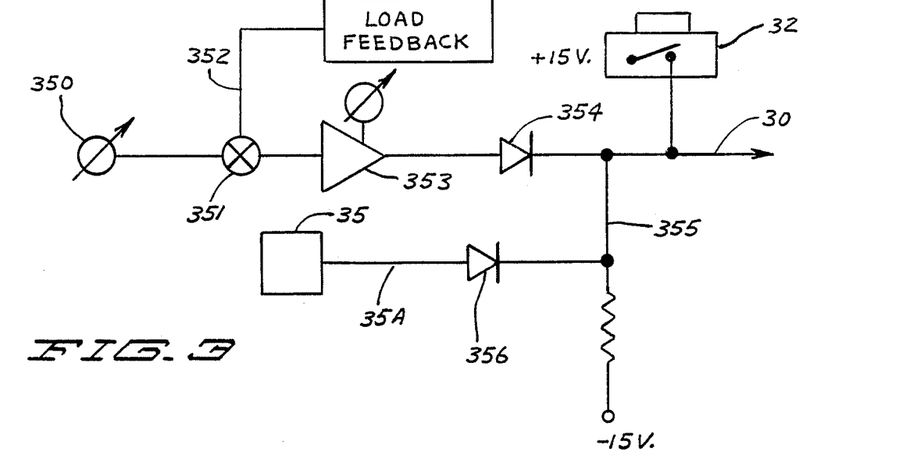
FIG. 3 is a schematic representation of a typical anti-compression circuit.

An additional feature is the anticompression gate 31, which is shown and explained in detail in FIG. 3. Placing the anticompression and/or antitension gates into the servo-control loop is a feature that can be applied to any controller, and not just a cascade controller of the present form.

Also, suitable specimen break detectors can be provided on the specimen in a conventional manner to shut off the test when a break has been detected.

Figure 4:
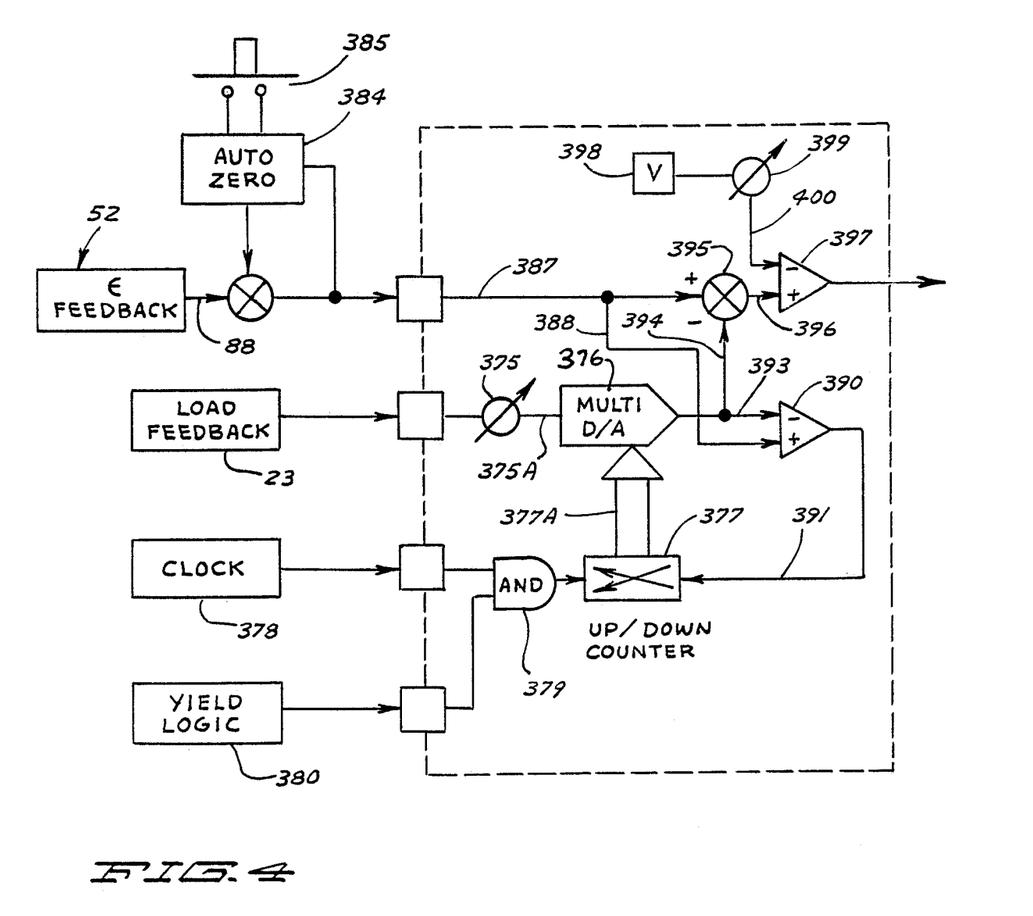
FIG. 4 is a schematic representation of an automated circuit used for determining when yield of a specimen is reached and providing a logic signal when post yield elongation of the specimen exceeds a desired amount.

The switch 35 is a manual switch, and it can be seen that it can be switched to provide for straight strain control, by connection to terminal 151, and straight load control by switching to terminal 150, where the switch is returned when it is started up. Switch 35 can also be connected to a terminal 153 that can provide external outputs of any type that is desired from control 154. Additionally, the present device can include a circuit such as that shown in FIG. 4 to provide a sufficient offset voltage to the strain signal to ensure that the specimen strain will be elongated typically 0.2 percent beyond its elastic elongation at yield before the system switches over to moving the actuator rapidly to break the specimen. Such a circuit as shown at FIG. 4 can be used with the circuit 215.

Figure 2:
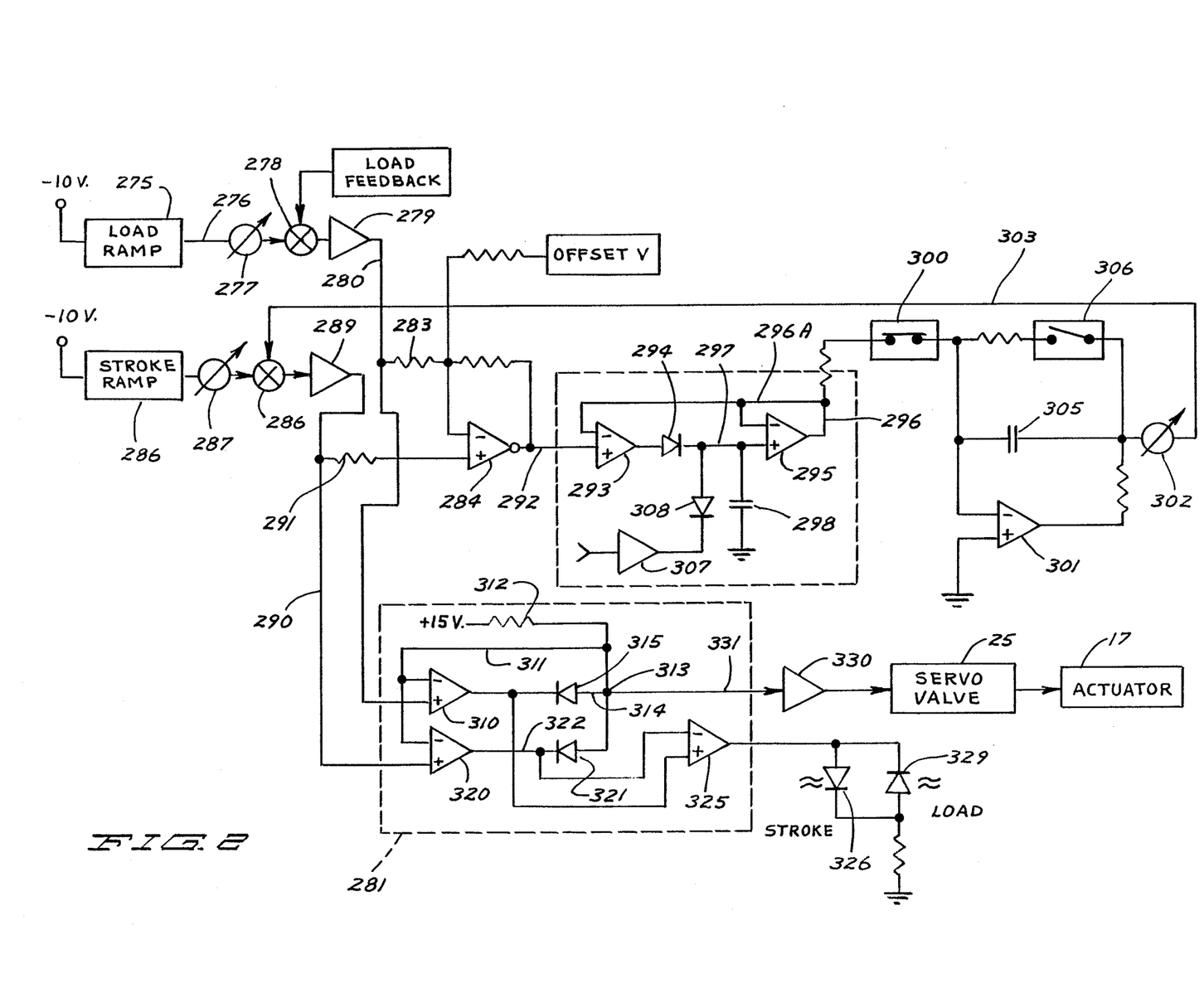
FIG. 2 is a schematic representation of a simplified form of the invention.

In situations where simplified circuitry is desired, and for tensile test control only where one can change from load to a stroke mode of control when the yield point has been reached, that is, when the specimen being tested has elongated under tensile loads a desired amount, the test can be finished up by changing to stroke control and speeding up movement to the test finish. The cascade load control is not used with this modified form, as shown in FIG. 2. The load feedback source is not shown, but is represented only as a block, as are the ramp generators used.

The circuit shown in FIG. 2 provides normal initial test control using the load controller, and a secondary control loop that is a function of the load control ramp signal combined with a signal that is a function of the velocity of the actuator used for applying the tensile load, and having both a load controller and a stroke controller in circuit. The load controller and stroke controller are conventional, servo-hydraulic control systems and the concept of transferring from one type of control to another during testing is described earlier. Basically, a load controller uses an input signal that programs the desired load with respect to time and uses a load feedback signal from the actuator. The stroke controller uses a desired stroke program and stroke (displacement) feedback signal. Both the load controller and the stroke controller are connected through a mode switch gate that causes the stroke controller to control the test functions at a "not to exceed" minimum latched velocity when the load program has reached the specimen yield and the actuator displacement begins to accelerate. Later, when in stroke control, the stroke control ramp can provide an increasing retraction stroke rate to accelerate specimen fracture after the yield point has been reached.

As shown in FIG. 2, a load ramp generator (providing the load program) indicated generally at 275 provides an output along a line 276 through a span control 277 and a summing junction 278 to a load controller amplifier 279. The load controller output drive is provided along a line 280, to one input of a mode control gate 281, which is an analog gate that senses drive signals at two inputs and provides a mode of control as a function of the relative value of the drive inputs. The gate can use conventional circuitry and the details will be explained later. Additionally, the output on line 280 is provided through a resistor 283 to an inverting input of an inverting amplifier 284.

A stroke ramp generator 286, which provides the command signal for stroke control, is connected through a span control potentiometer 287 to a summing junction 288. The output of summing junction 288 is connected to a stroke controller amplifier 289, which has an output line 290 (the output of the stroke controller) also connected to one of the inputs of mode control gate 281. The output line 290 of the stroke amplifier is further connected through a resistor 291 to the non-inverting input of the inverting output amplifier 284.

The amplifier 284 provides an inverted output that is proportional to the difference between the load controller output drive on line 280 and the stroke controller output drive on line 281, and since amplifier 284 has an inverting output the output will be positive when the load controller output signal is larger than the output signal from the stroke controller.

Amplifier 284 is a very high gain amplifier so that the signal on the output line 292 of amplifier 284 is very high even when there is very little difference in the load controller output signal and the stroke controller output signal on lines 280 and 290, giving accurate tracking integrator following. Note that a suitable feedback signal resistor is provided from line 292 to the inverting input of the amplifier 284.

The output from the amplifier 284, via line 292, is connected to the non-inverting input of an amplifier 293 that has its output connected through a diode 294 to the non-inverting input of an amplifier 295. The output of amplifier 295 on line 296 is fed back to its inverting input, and also to the inverting input of amplifier 293 with a line 296A. The line 297 on the output of diode 294 is coupled to circuit common (ground) through a capacitor 298 that provides a biasing signal that represents a minimum latched velocity of the stroke of the test actuator and which provides a reference signal at the time yield of the specimen 18 (FIG. 1B) occurs and the drive input to the servo-valve switches sources, namely from load control used for conducting the test up to the desired elongation after yield, to stroke control to break the specimen.

The output line 296 is connected through a switch 300 (it is a solid state switch) to the inverting input of a tracking integrator amplifier 301, which has its output connected through a gain control potentiometer 302 along a line 303 that is fed back to the displacement summing junction 286 at the input of the stroke control amplifier 289. The output of the tracking integrator amplifier 301 is summed with the stroke command ramp signal from span control 287. When in the tracking mode, the input to integrator 301 is proportional to the velocity of the actuator that is deforming the specimen in tension. The test specimen 18 is mounted as shown in FIG. 1, where the retraction of the actuator 17 loads the specimen in tension, and thus the velocity of retraction of the actuator is considered to be positive velocity. The velocity signal is latched at its (least positive or most negative) value by amplifiers 293, 295 and capacitor 298. The signal on line 292 (the output from inverting differential amplifier 284) represents the difference between load and stroke controller drives, and this signal is integrated to provide the tracking displacement signal. Thus, the actual actuator velocity signal is a derived signal from the input to the tracking integrator.

A second switch 306 is provided, but is only for resetting the system, and when a reset signal is provided to an input of an amplifier 307 on the output side of diode 294, and through a diode 308, the resulting reset signal recharges or resets capacitor 298, generally at the end of a run.

As long as the velocity of the actuator stays the same or is decreasing, the signal provided on the output of amplifier 295 remains at a static condition, providing feedback to the stroke controller that keeps the output high, and the analog gate mode switch 281 will be kept in its load control mode.

Referring now to the analog control gate or switch outlined at 281 in dotted lines, it includes a first amplifier 310 that has its non-inverting input connected to the load controller output line 280, and its inverting input is connected to a 15 volt D.C. source along a line 311, through a resistor 312. This line 311 is also connected at 313 to the output line 314 from the amplifier 310. A diode 315 is connected between the junction 313 and the output of the amplifier 310, and is oriented to conduct negative voltages from the amplifier.

A second amplifier 320 has its non-inverting terminal connected to the output line 290 of the stroke controller 289, and also has its inverting input terminal connected to line 311, and thus to the 15 volt source and to the junction 313. The output of the amplifier 320 is connected to junction 313 through a reverse diode 321 in line 322 leading from the amplifier 320.

The outputs of amplifiers 310 and 320 are connected to a comparator 325 which will cause one of a pair of light emitting diodes to light. These LEDs comprise a stroke indicating light emitting diode 326 or a load indicating light emitting lighting diode 327. The LEDs 326 and 327 are connected to circuit common as shown, and are connected in opposite directions so that the LEDs will indicate which amplifier of the gate is in control and thus what mode is instantaneously being used for control.

The lines 280 and 290 form the input to gate 281, and whichever signal is less (least positive or most negative) will be the signal that is selected and will show up on the output junction 313 because of the control of the diodes 315 or 321. The junction 313 as shown is connected to drive a servo-valve amplifier 330. The servo-valve amplifier 330 will be driven to retract the actuator when a positive signal is present on junction 313 and on the input line 331 to amplifier 330.

As stated previously, for initial loading, as long as the actuator velocity is maintained at the same rate or is decreasing, load control will remain the control mode function, and the servo-valve will be controlled in proportion to the signal on line 280. However, as soon as the load controller has to accelerate the actuator in order to keep the load feedback tracking the programmed load ramp input, the stroke feedback signal, acting through the summing junction 286 and through the high gain of amplifier 284, almost immediately locks the system onto the minimum velocity latch signal from capacitor 298 and the tracking integrator 301 which is now a programming ramp generator, keeps increasing in output only very slowly.

The stroke controller output drive signal on line 290 will now call for less tensile deformation (less voltage) than will the load controller, which has a decreasing feedback and thus the output on line 280 is increasing. The load controller wants to add more tensile deformation because at the yield point of the specimen the actuator cannot maintain the load signal that its ramp is calling for in relation to the feedback load signal when it is latched at its minimum latched velocity. At this point, the gate 281, and in particular the amplifier 320 will sense that the stroke controller calls for less tensile loading (less retraction speed) then does the load controller, and will cause the mode switch to occur in that the output of amplifier 320 will be more negative than the output of amplifier 310, and the diode 321 will cause the drive signal source at valve amplifier 330 to switch to be a function of and track the stroke controller output signal on line 290.

Once in the stroke control modes, suitable controls can be used for opening switch 300, so that the ramp generator 286 can be used for ramping up a stroke as desired for quickly fracturing the specimen after the required amount of plastic deformation for a standard tensile test has occurred.

Normally, the operator does not stop the test until the specimen is fractured. In the test sequence, initially there is a loading ramp, represented as a ramp voltage on line 280. Then when yield occurs, a second test phase begins in which there is a latching of the minimum velocity through the diode 294, amplifiers 293 and 295, and capacitor 298. In the third phase of the test is when the mode switch occurs from the minimum velocity latch from load control to stroke control to accelerate the fracture of the specimen. The minimum velocity, again, is represented by the value of the voltage that is stored at the capacitor 298.

In both forms of the invention described, the system circuit desirably prevents the specimen from being placed into more than a very low level of compression load. Generally, the specimen can take a slight compression, but if, for example, a large compression load signal is commanded accidently, an anti-compression gate shown in FIG. 1B at 31 becomes operative to prevent damage to the specimen. The output of switch 35 is connected to the anti-compression gate input, and the anticompression gate output is coupled to the servo-valve amplifier.

The anti-compression gate 31 of FIG. 1B has an input potentiometer 350 (see FIG. 3) that comprises a voltage source and which permits setting a desired voltage level that represents a certain "never exceed" amount of compression loading that can be exerted. For example, approximately −0.5 volts could be used as a setting which would lead from source 350 into a summing junction 351, and which is summed with a load feedback signal on line 352, and is the load feedback signal from load cell 23. The output of summing junction 351 is connected through a suitable amplifier 353, that is connected to a diode 54. The diode 354 is biased on its output side with a −15 volt source through a line 355. The normal value command input line 35A to gate 31 from switch 35 is connected to a diode 356 which is also biased by the same −15 volt source from line 355. The output from the gate is along line 30, as shown. The most positive signal will be the one that will be selected on the output line 30, as shown by the connections of the gate in FIG. 3, and as long as the output from the switch 35 is more positive than the compression controller output signal (from 353), then the signal on line 30 will be from the switch 35. If the output from the switch 35 gets less positive than the allowable compression, control defaults to the anticompression controller 350 and a negative voltage limited to −0.5 volts will be connected for controlling the servo-valve, to prevent crunching the specimen under high compression loads. This is a simplified selector gate which will select either the output from the switch 35, or the output from the controlling potentiometer 350, that can be set by the operator to provide the maximum compression that can even be applied to the specimen.

ASTM test specifications require that tensile test specimens be elongated 0.2 percent beyond their yield point in order to standardize the tests. During this 0.2 percent elongation beyond yield point the specimen will have some elastic strain, and some plastic or yielding strain. The operator must insure that the test continues under a predictable and stable mode of control during this required standard elongation after yield point.

Once the specimen has yielded this 0.2 percent, the specimen can be fractured quickly. Thus, after 0.2 percent elongation beyond yield the system can then go into stroke control. To at least provide the 0.2 percent elongation, a control is provided such as the circuit in FIGS. 1A and 1B.

Referring now specifically to FIG. 4, the amount of offset voltage can be determined for individual tests, but a typical example is that a 0.2 percent elongation will be equal to approximately 0.4 volts change in strain signal on a typical tensile test specimen. The system of FIG. 4 receives a signal from the load cell 23, which is the load feedback signal, and passes it through a ranging potentiometer 375, the output signal of which is fed to the input of multiplying digital-to-analog converter 376 along a line 375A.

The multiplying digital-to-analog converter 376 is controlled by an up-down counter 377. The up-down counter has a clock input source 378 coupled through an AND gate 379. AND gate 379 has a second input from a logic circuit 380 called the yield logic that indicates whether the test specimen is still in its elastic range and has not reached the yield point. The logic circuit 380 can be any desired converter circuit set for a particular specimen and compares the slope of a load to stroke line, so when the relationship of stress to strain is beyond the yield point for the material and thus no longer linear, the logic circuit provides an output. The AND gate 379 permits the clock pulses to enter the up-down counter until the yield point has been reached, at which time the logic circuit 380 blocks further clock pulses from being sent to the up-down counter 377.

The determination of strain is provided by the extensometer signal from the extensometer feedback signal from conditioning circuit 52 along line 88. The voltage signal on line 88 is passed into a summing junction 383 which also receives an input from an automatic strain zeroing circuit 384 of conventional design that is manually operated with a push button 385 that can be used at the initialization of the test to zero the offset circuit.

The voltage from the extensometer is provided along line 387, and represents a signal proportional to elongation of the specimen from the extensometer 50 in FIG. 1, for example.

A line 388 is connected between line 387 and the non-inverting input of a comparator 390. The output of the comparator 390 is provided along a line 391 to the input of the up-down counter 377. The up-down counter 377 is connected through a bus 377A to the input of the multiplying digital analog converter. The output of the multiplying digital-to-analog converter along a line 393 is connected to the inverting input terminal of comparator 390. It is also connected through a line 394 to a negative input of a summing junction 395 that has a positive input connected to line 387 The summing junction 395 can include means to provide a desired gain to its output comprising the difference signal.

The output of the summing junction 395 is connected along a line 396 to a non-inverting input of a second comparator 397, which has its inverting terminal connected with a line 400 to a voltage source 398 that can be adjusted with a potentiometer 399 to provide the offset voltage. For typical tests, the voltage from source 398 will be in the range of 0.4 volts, as previously stated.

In operation, the output of the multiplying digital-to-analog converter along line 393 is selected to be a fraction of the input load cell signal on line 375A depending on the digital word from the up-down counter that is being placed into the control input of the multiplying digital-to-analog converter. The comparator 390 merely compares the output of the digital-to-analog converter on line 393, which is a voltage signal proportional to load with the signal on line 387, which is the voltage from the extensometer. If the signal from the extensometer feedback on line 387 is larger than the signal on line 393, the output of comparator 390 is positive. This causes the up-down counter 377 to increment positively whenever a clock pulse comes into the counter. The comparator monitors the difference at its inputs, and if the voltage from the extensometer is smaller than the digital-to-analog converter output, which is again a portion of the load signal, the comparator output is low and the counter will decrement or count down when a clock pulse is received. There would be, therefore, a series of "tries" or comparisons at the clock pulse rate until the signal on line 393 and the signal on line 388 are at a known, preselected ratio to each other as determined by the comparator. These same signals on lines 393 and 387 are also summed at the summing junction 395, and as shown, when the signals are equal there would be no output along line 396, as long as the clock signals are being received by the up-down counter.

The yield logic 380 can be a standard logic circuit that independently compares the load cell signal and the signal from the extensometer to determine that the specimen is still in its elastic range. Once a yield point was reached, the logic signal from logic 380 blocks the AND gate 379 from passing further clock signals, and the counter keeps the output from multiplying digital-to-analog converter the same as when yield occurs.

Thereafter, as long as the extensometer signal on line 387 became larger in relation to the fixed fraction of the load cell signal along line 394 (from multiplying digital-to-analog converter 376), there is a positive output on line 396, and the logic circuit 380 will indicate the specimen is in its plastic deformation range.

In the situation given as an example, where 0.4 volts would equal at least 0.2 percent elongation of the specimen beyond yield point, the comparator 397 provides an output when the signal on line 396 equals the signal from the voltage source 398 received at the inverting input terminal of comparator 397. Thus, when the output of the summing junction 395 equals 0.4 volts (based on the increasing signal from the extensometer), the output from comparator 397 will indicate that the specimen has been yielded at least 0.2 percent beyond its yield point.

The output from load cell 23, which indicates the actual load on the specimen, is fractioned by the multiplying digital-to-analog converter and kept equal to the extensometer feedback signal until the logic circuit 386 indicates the yield point has been reached. The comparator 397 will not provide an output until the extensometer signal is essentially 0.4 volts different from the load feedback signal at the yield point. Stated another way, as the extensometer voltage feedback signal increases to be greater than the load feedback signal at yield, then the extensometer signal indicates that there is an elongation of the specimen in the plastic range and there would be a positive output from the summing junction 395 when the extensometer feedback signal increases to equal the preselected offset voltage from source 398.

The control circuits increase accurate and reliable tensile tests, with adequate safety features for protection of valuable specimens.

Although the present invention has been described with reference to preferred embodiments, workers skilled in the art will recognize that changes may be made in form and detail without departing from the spirit and scope of the invention.

What is claimed is:

1. A control system for testing specimens in tension utilizing an actuator that moves to load the specimen in tension in response to servo-control signals, and including means to provide a first feedback signal proportional to the load on the specimen, and a second feedback signal proportional to the stroke position of the actuator comprising:

first circuit means including a load controller and a stroke controller, each having a separate program for providing command input signals on the basis of time, means to provide said first feedback signal to said load controller, and means to provide said second feedback signal to said stroke controller, the load and stroke controllers each providing an output signal;

second circuit means for providing a control signal to the actuator which is a function of the load controller output signal during elastic deformation of the specimen being tested, and including means for switching the control signal to the actuator to be a function of the stroke controller output signal after yield of the specimen has been reached; and third circuit means coupled to the first circuit means for preventing increasing velocity of the actuator prior to operation of the means for switching.

2. The system of claim 1 including means to provide an offset voltage signal to maintain at a set level the load controller output signal until the actuator has been operated to elongate the specimen a desired amount after the yield point of the specimen has been reached.

3. The system as specified in claim 1 and fourth circuit means coupled to the second circuit means and including means deriving a signal from an extensometer measuring strain directly on the specimen, said fourth circuit means being selectable to provide a strain related signal representing a function of specimen strain to the load controller output in place of the load related signal.

4. The system as specified in claim 3 wherein said fourth circuit means includes gate means responsive to signals which combine strain measurement signals with each of said load and stroke controller output signals to supervise the strain related signal and default to appropriate load related signals upon occurrence of a preselected condition.

5. The system as specified as specified in claim 1 wherein one of said first, second, and third circuit means includes gate means to sense the respective values of a function of the load controller output signal and a signal which is a function of a preset signal representing a desired velocity of the actuator, and to select one of such load controller output signal and preset signal as the signal provided to control the actuator, depending on the relative values of such load controller output signal and preset signal.

6. The system as specified in claim 1 wherein the system includes second switch means to provide a load related signal to control the actuator to prevent the stroke controller from being placed in control until the actuator has been controlled to apply a load to the specimen.

7. The system of claim 1 wherein said stroke controller provides a completion control signal that accelerates the movement of the actuator and the fracture of a specimen being tested after the completion control signal is placed in control.

8. The system as specified in claim 1 wherein said system includes means to provide an offset voltage signal to prevent the control signal which is a function of the load controller output signal from being switched from control of the actuator until a specimen being tested has been elongated a desired amount beyond its yield, the last mentioned means being responsive to a signal indicating the strain in the specimen.

9. The system as specified in claim 1 wherein said first feedback signal comprises a load feedback signal and anti-compression circuit means operable as a function of said load feedback signal to provide a signal to the first circuit means which maintains the control signal at a desired level regardless of the value of other control signals.

10. The control system of claim 1, wherein said first circuit means includes means associated with the stroke controller that causes the output signal of the stroke controller to accelerate the actuator to cause fracture of the specimen, after the means for switching is operated to provide the control signal to the actuator to be a function of the stroke controller output signal.

11. A test control system for testing specimens utilizing an actuator that moves to load the specimen along a specimen axis in response to servo-control signals comprising:
a first circuit means including controller means coupled to the system for providing selectable input control signals for the actuator on the basis of time and means to provide a load feedback signal indicating load on the specimen and a displacement feedback signal indicating displacement of the actuator;
second circuit means coupled to the controller means for providing a first input control signal to the actuator, which is a function of load during loading in an elastic loading of said specimen along the specimen axis in one direction; and
antireversal circuit means operable as a function of the load feedback signal to provide a signal to the first circuit means to prevent loading the specimen in direction along the specimen axis opposite from the one direction more than a desired amount.

12. The system of claim 11 and third circuit means coupled to the controller means to provide a second input control signal to the actuator which is a function of actuator displacement and which controls actuator displacement, and means in the controller means for switching to control the displacement of the actuator using the second input control signal after the specimen being tested has yielded.

13. The system of claim 12 and fourth circuit means coupled to the first circuit means for preventing excessive velocity of the actuator prior to operation of the means for switching.

14. The system of claim 11 including means for providing a signal to maintain at a set level the first input control signal to control the actuator until the actuator has been operated to elongate the specimen a desired amount.

15. A control system for testing specimens in tension utilizing an actuator that moves to load the specimen in response to servo-control signals comprising:
first circuit means including a load controller and a stroke controller, each being responsive to a separate program providing input signals on the basis of time, means to provide a first feedback signal to said load controller, and means to provide a second feedback to said stroke controller whereby said first circuit means provides a separate load error signal and a separate stroke error signal;
second circuit means for providing a first control signal to the actuator which is a function of the load error signal during elastic deformation of said specimen, and including means for switching to a second control signal to the actuator which is a function of the stroke error signal upon acceleration of the actuator after yield of the specimen being tested has been reached; and
third circuit means coupled to the first circuit means and including a signal generator providing a signal representing a loading velocity for input to the stroke controller for preventing increasing velocity of the actuator beyond a desired velocity.

16. The system as specified in claim 15 wherein said third circuit means includes gate means to sense the respective values of the load error signal and the stroke error signal the gate means being operable to select one of the load and stroke error signals as the signal provided to control the actuator, depending on the relative values of such load and stroke error signals.

17. A control system for testing specimens in tension utilizing an actuator that moves to load the specimen in tension in response to servo-control signals, including means to provide a first feedback signal which is a function of the load on the specimen, means to provide a second feedback signal which is a function of the stroke position of the actuator, a first controller, means for providing a first input signal to the first controller, the first controller providing a first output load control error signal representing a function of the first feedback signal and the first input signal; a stroke controller, means to provide a stroke input signal to the stroke controller, said stroke controller providing an output signal which is a function of the second feedback signal and the stroke input signal; means to selectively provide the first controller output signal and the stroke controller output signal to control the actuator, said means to selectively provide being operable for providing the first output load control error signal to the actuator upon initial loading of the specimen, and having means for switching to provide the stroke controller output signal to the actuator in place of the first output load control error signal; and means coupled to the means to selectively provide for preventing an increase of the velocity of the actuator prior to the operation of the means for switching.

18. The system of claim 17 wherein means are provided for preventing the means for switching from operating to supply the stroke controller output signal to the actuator until subsequent to a selected amount of elongation of the specimen under plastic deformation.

* * * * *